United States Patent [19]

Gladwin

[11] 4,241,225

[45] Dec. 23, 1980

[54] PREPARATION AND DEHYDROGENATION OF CYCLOALKANOL DERIVATIVES

[75] Inventor: Keith Gladwin, Chesterfield, England

[73] Assignee: Coalite and Chemical Products Limited, North Chesterfield, England

[21] Appl. No.: 913,127

[22] Filed: Jun. 6, 1978

[30] Foreign Application Priority Data

Jun. 8, 1977 [GB] United Kingdom ............... 23926/77

[51] Int. Cl.$^3$ .......................................... C07C 179/02
[52] U.S. Cl. .................... 568/652; 568/670; 564/300; 564/443; 564/1
[58] Field of Search ................ 260/563 R; 568/652, 568/670

[56] References Cited

U.S. PATENT DOCUMENTS

| Re. 29,200 | 5/1977 | McKague et al. | 568/652 |
| Re. 29,201 | 5/1977 | McKague et al. | 568/652 |
| 2,500,016 | 3/1950 | Allenby | 568/670 X |
| 2,812,358 | 11/1957 | Schlichting et al. | 568/670 X |
| 3,879,464 | 4/1975 | Kalopissis et al. | 260/563 R UX |

OTHER PUBLICATIONS

Morrison & Boyd, "Organic Chemistry", 3rd Ed., Allyn & Bacon, Inc., Boston (1973), p. 565.

Primary Examiner—Paul F. Shaver
Attorney, Agent, or Firm—Blanchard, Flynn, Thiel, Boutell & Tanis

[57] ABSTRACT

Alkanols, alkylamines or hydroxylamines are reacted with a cycloalkene oxide in the presence of Fuller's earth as a catalyst to prepare, respectively, 2-cycloalkanol ethers, 2-alkylamino-cycloalkanols, or 2-hydroxylamino-cycloalkanols.

5 Claims, No Drawings

PREPARATION AND DEHYDROGENATION OF CYCLOALKANOL DERIVATIVES

The present invention relates to the preparation of 2-cycloalkanol ethers, 2-cycloalkylamines and 2-hydroxylamino-cycloalkanols.

According to the invention, there is provided a method of preparing a 2-cycloalkanol ether, a 2-alkylamino-cycloalkanol or a 2-hydroxylamino-cycloalkanol, comprising reacting on alkanol, an alkylamine or hydroxylamine with a cycloalkene oxide in the presence of a catalyst selected from mineral acids, other acids, ion exchange resins, acidified earths and acidic salts, the reaction proceeding in accordance with the following equation

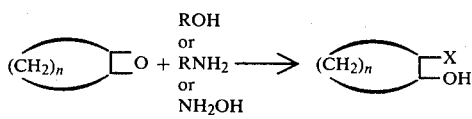

where n represents an integer, — X represents —OR, —NHR or —NHOH and R represents a substituted or unsubstituted alkyl, aryl or aralkyl residue.

The alkyl group of the alkanol or alkylamine may be substituted or unsubstituted. The alkanol or alkylamine may have a primary, secondary or tertiary alkyl group attached to the —OH or —NH$_2$ group. The alkyl group may have, for example, up to twelve carbon atoms and may be a straight chain alkyl group or a cycloalkyl group.

The cycloalkyl group of the cycloalkene oxide may be substituted or unsubstituted and preferably contains 5 to 12 carbon atoms in the ring.

When, in accordance with the method of the invention, an alkanol is reacted with a cycloalkene oxide, the reaction products comprise predominantly a 2-cycloalkanol ether.

When, in accordance with the method of the invention, an alkylamine is reacted with a cycloalkene oxide, the reaction products comprise predominantly a 2-alkylamino-cycloalkanol.

When in accordance with the method of the invention, hydroxylamine is reacted with a cycloalkene oxide, the reaction products comprise predominantly a 2-hydroxylamino-cycloalkanol.

The cycloalkene oxide may be a substituted cyclohexene oxide or unsubstituted cyclohexene oxide i.e. cyclohexene oxide itself.

The alcohol may be isopropanol.

In a preferred form of the invention, the cycloalkene oxide is cyclohexene and the alcohol is isopropanol, the 2-cyclohexanol ether produced being 2-isopropoxy cyclohexanol.

The rate of reaction is strongly dependent on the concentration of the catalyst and at certain concentrations of the catalyst is practically instantaneous.

Temperatures up to the reflux temperature of the reaction mixture may be used.

The alkanol, alkylamine or hydroxylamine is conveniently used in excess compared with the cycloalkene oxide. Preferably the mole ratio of the alkanol, alkylamine or hydroxylamine to the cycloalkene oxide is initially at least 10:1, more preferably at least 15:1 and may be up to or may exceed 25:1. We have found that where the mole ratio of the alkanol, alkylamine or hydroxylamine to the cycloalkene oxide is at least 20:1 2-cycloalkanol ether, 2-alkylamino-cycloalkanol or 2-hydroxylaminocycloalkanol may be obtained in a yield, based on the cycloalkene oxide, greater than 90%.

The reaction between the alkanol, alkylamine or hydroxylamine and the cycloalkene oxide may be carried batchwise or continuously. In one preferred form of the invention, the cycloalkene oxide is refluxed with excess of the alkanol, alkylamine or hydroxylamine in the presence of the catalyst. In an alternative preferred from of the invention, the cycloalkene oxide, excess of the alkanol, alkylamine or hydroxylamine and the catalyst are continuously fed into a reactor, and unreacted alkanol, alkylamine or hydroxylamine is separated from the product discharging from the reactor and is recycled to the reactor.

The catalyst is preferably an acidified earth such as Fullers' earth or, when the method is carried out batchwise, a mineral acid such as sulphuric acid. Alternatively the catylyst may be an acidic salt such as ammonium chloride.

The 2-cyclohexanol ether, 2-alkylamino-cycloalkanol or 2-hydroxyl-amino-cyclohexanol prepared as described above may be dehydrogenated to produce an ortho-substituted phenol. The dehydrogenation may be carried out over a palladium, platinum or other noble metal catalyst in the liquid or vapour phase. Preferably the dehydrogenation is carried out over a palladium catalyst and in the presence of sulphur and sodium carbonate. The hydrogenation may be represented by the following equation:

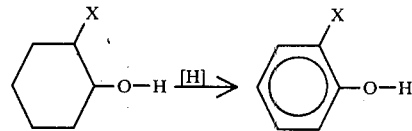

where —X represents —OR, —NHR or —NH$_2$OH and R represents an alkyl, aryl or aralkyl residue.

Where the initial cycloalkene oxide is cyclohexene oxide and the initial alcohol is isopropanol, the phenolalkyl ether (or catechol monoether) produced is o-isopropoxyphenol. This compound is useful in the manufacture of the compound which is used as a pesticide and which is an active ingredient of the pesticidal composition "Baygon" and the pesticidal composition "Propoxur".

The invention is illustrated by the following examples.

EXAMPLE 1

Cyclohexene oxide (9.8 g, 0.1 mole) was added dropwise to a refluxing mixture of isopropanol (2 moles) in which was suspended acidified Fullers' earth (Fulcat 22B) (1% w/w) as catalyst. Immediately thereafter the catalyst was removed by filtration and the product was stripped of isopropanol by distillation. The residue was fractionated to yield 13.3 g of 2-isopropoxy cyclohexanol (yield 90% based upon cyclohexene oxide).

EXAMPLE 2

Isopropanol and Fulcat 22B were continuously blended in a feed vessel which was allowed to overflow continuously into a reactor into which was continuously metered cyclohexene oxide. The overflow from the blending vessel and the cyclohexene oxide feed were adjusted such that the mole ratio of isopropanol to cyclohexene oxide was 20:1.

The reaction time, i.e. the residence time of the cyclohexene oxide in the reactor, was less than 30 minutes.

The reaction mixture was allowed to overflow continuously from the reactor and was filtered, the Fulcat 22B being returned to the feed vessel until it has passed three or four times through the reactor. The filtrate was continuously distilled to remove isopropanol which was returned to the feed vessel. The residue was fractionated to separate 2-isopropoxy cyclohexanol in 93% yield based upon the cyclohexene oxide.

EXAMPLES 3 to 9

Example 2 was repeated using various alcohols instead of isopropanol. The results are summarised in the table below. The reaction time was less than 30 minutes in each case.

| Example No. | Alcohol | Mole ratio (Alcohol/ oxide) | Yield of product (2-alkyloxy cycloalkanol) % | Purity (%) | B.p. °C. | (at stated pressure) |
|---|---|---|---|---|---|---|
| 3 | Methanol | 3.3:1 | 82 | 98 | 81–82 | 13mm Hg |
| 4 | Ethanol | 3.3:1 | 84 | 98 | 86 | 20mm Hg |
| 5 | sec-butanol | 3.3:1 | 72 | 98 | 85–90 | 5mm Hg |
| 6 | pentanol | 3.3 | 92 | 98.7 | 95 | 5mm Hg |
| 7 | octanol | 3.3 | 86 | 94 | 120 | 5mm Hg |
| 8 | decanol | 3.3 | 90 | 97.2 | 135 | 5mm Hg |
| 9 | cyclohexanol | 3.3 | 75 | 95 | — | — |

EXAMPLE 10A

A mixture of 2-isopropoxy cyclohexanol prepared as described in Example 1 and diphenyl was introduced into a reaction vessel. Then a palladium-on-carbon (porous charcoal) catalyst comprising 3% by weight palladium was added to the reaction vessel. Then a solution of diphenyl sulphide in further of the 2-isopropoxy cyclohexanol was added to the reaction vessel, followed by powdered sodium carbonate (anhydrous). In the resulting reaction system, the volume ratio of 2-isopropoxy cyclohexanol to diphenyl was 1:1, the concentration of sulphur (as diphenyl sulphide) was 18 ppm, and the concentration of $Na_2CO_3$ was 1% by weight. The reaction system was refluxed (at 210°–220° C.) whilst a stream of nitrogen was passed through the system. When hydrogen ceased to be produced (after 25 hours) the reaction system was cooled and treated with an aqueous solution of sodium hydroxide to extract a product comprising isopropoxyphenol. This product consisted of (by weight):

| Isopropoxyphenol | 95.5% |
|---|---|
| Phenol | 3.8% |
| Catechol | 0.7% |

The isopropoxyphenol was produced in a yield of about 72.5% based on the isopropoxy cyclohexanol.

EXAMPLE 10B

Example 10A was repeated using 2-isoproxy cyclohexanol prepared as described in Example 2. Substantially identical results were obtained.

EXAMPLES 11A and 11B

Examples 10A and 10B were repeated, the concentration of sulphur (as diphenyl sulphide) in the reaction system being 24 ppm and production of hydrogen ceasing after refluxing of the reaction system for 21 hours, all other conditions being the same as previously described.

The product consisted of (by weight):

| Phenol | 1.4% |
|---|---|
| Catechol | 0.4% |
| Diphenyl | 0.2% |
| 2-isoproxy cyclohexanol | 0.2% |

The isoproxyphenol was produced in a yield of 83% based on the isopropoxy cyclohexanol.

In examples 10A to 11B above, it is envisaged that the isopropoxyphenol could have been separated from the reaction system by distillation since substantially no impurities are produced as by products.

I claim:

1. A method of preparing 2-isopropoxy cyclohexanol, comprising: reacting a stoichiometric excess of isopropyl alcohol with cyclohexene oxide, in the presence of a catalytically effective amount of acidified Fuller's earth until 2-isopropoxy cyclohexanol is formed, and then recovering the 2-isopropoxy cyclohexanol from the reaction mixture.

2. A method according to claim 1, wherein the mole ratio of isopropanol to cyclohexane oxide is at least 10:1 initially.

3. A method of producing ortho-isopropoxyphenol, comprising: catalytically dehydrogenating the 2-isopropoxy cyclohexanol prepared according to claim 1.

4. A method of preparing 2-isopropoxy cyclohexanol, consisting essentially of: adding cyclohexene oxide to a suspension consisting essentially of a catalytically effective amount of acidified Fullers' earth suspended in isopropanol, to form a reaction mixture wherein the mole ratio of isopropanol:cyclohexane oxide is at least 20:1, and maintaining the reaction mixture at about the reflux temperature of the reaction mixture until 2-isopropoxy cyclohexanol is formed; and then filtering the reaction mixture to separate said acidified Fullers' earth and distilling off unreacted isopropanol and thereby recovering said 2-isopropoxy cyclohexanol.

5. A method of producing ortho-isopropoxyphenol, comprising reacting isopropanol with cyclohexene oxide, in the presence of a catalytically effective amount of acidified Fullers' earth as catalyst, the alcohol being present in excess compared with the cyclohexene oxide, whereby 2-isopropoxy cyclohexanol is formed; separating the 2-isopropoxy cyclohexanol; and catalytically dehydrogenating the 2-isopropoxy cyclohexanol to yield the ortho-isopropoxyphenol.

* * * * *

UNITED STATES PATENT OFFICE
CERTIFICATE OF CORRECTION

Patent No. 4 241 225           Dated December 23, 1980

Inventor(s) Keith Gladwin

It is certified that error appears in the above-identified patent and that said Letters Patent are hereby corrected as shown below:

Column 4, line 43;    change "cyclohexane" to

---cyclohexene---.

Column 4, line 53;    change "cyclohexane" to

---cyclohexene---.

Signed and Sealed this

Seventeenth Day of March 1981

[SEAL]

Attest:

RENE D. TEGTMEYER

Attesting Officer      Acting Commissioner of Patents and Trademarks